(12) United States Patent
Kambara

(10) Patent No.: US 11,406,798 B2
(45) Date of Patent: Aug. 9, 2022

(54) GUIDE WIRE

(71) Applicant: TERUMO KABUSHIKI KAISHA, Tokyo (JP)

(72) Inventor: Kayo Kambara, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 424 days.

(21) Appl. No.: 16/151,668

(22) Filed: Oct. 4, 2018

(65) Prior Publication Data

US 2019/0262588 A1    Aug. 29, 2019

(30) Foreign Application Priority Data

Feb. 26, 2018 (JP) .............................. JP2018-032453

(51) Int. Cl.
*A61M 25/09* (2006.01)

(52) U.S. Cl.
CPC ..... *A61M 25/09* (2013.01); *A61M 2025/0915* (2013.01); *A61M 2025/09091* (2013.01); *A61M 2025/09133* (2013.01); *A61M 2025/09175* (2013.01); *A61M 2205/0216* (2013.01)

(58) Field of Classification Search
CPC ........ A61M 25/09; A61M 2025/09083; A61M 2025/09091; A61M 2025/09133; A61M 2025/0915; A61M 2025/09175; B21F 3/08; B21L 1/00; B21L 1/02; B21L 1/04; B21L 5/00; B21L 5/02; B21L 7/00; B21L 11/00; B21L 11/10; B21L 11/02; B21L 11/08; B21L 11/06; B21C 37/12; B21C 37/121
USPC ....................... 600/585; 72/146; 140/92, 124
See application file for complete search history.

(56) References Cited

U.S. PATENT DOCUMENTS

| 4,080,706 A | 3/1978 | Heilman et al. |
| 4,724,596 A * | 2/1988 | Pavlyak ................ B21C 37/121 138/135 |
| 4,955,384 A * | 9/1990 | Taylor ................... A61M 25/09 600/434 |

(Continued)

FOREIGN PATENT DOCUMENTS

| EP | 1 938 859 A1 | 7/2008 |
| EP | 2 762 188 A1 | 8/2014 |

(Continued)

OTHER PUBLICATIONS

The extended European Search Report dated Jul. 4, 2019, by the European Patent Office in corresponding European Patent Application No. 18213842.0-1132. (7 pages).
Office Action (Notice of Reasons for Refusal) dated Aug. 3, 2021, by the Japanese Patent Office in corresponding Japanese Patent Application No. 2018-032453 and an English Translation of the Office Action. (10 pages).

*Primary Examiner* — Daniel L Cerioni
*Assistant Examiner* — Deirdre M Willgohs
(74) *Attorney, Agent, or Firm* — Buchanan Ingersoll & Rooney PC

(57) ABSTRACT

A guide wire which is flexible in a distal portion and which can prevent occurrence of damage such as breakage and separation of a coil in the distal portion has an elongated core member and a tubular body located so as to cover a periphery of a distal portion of the core member. The tubular body is formed using a belt-shaped member wound in a spiral shape, and has an engagement portion which causes side portions adjacent in a longitudinal axis direction of the core member to engage with each other in the belt-shaped member.

18 Claims, 5 Drawing Sheets

(56) References Cited

U.S. PATENT DOCUMENTS

| | | | | |
|---|---|---|---|---|
| 5,465,733 A | * | 11/1995 | Hinohara | A61M 25/09 600/585 |
| 5,931,830 A | * | 8/1999 | Jacobsen | A61M 25/09 604/523 |
| 8,100,837 B1 | * | 1/2012 | Cornish | A61M 25/09 600/585 |
| 2003/0069522 A1 | | 4/2003 | Jacobsen et al. | |
| 2003/0105415 A1 | | 6/2003 | Mirigian | |
| 2004/0082881 A1 | * | 4/2004 | Grewe | A61M 25/09 600/585 |
| 2012/0191012 A1 | | 7/2012 | Chin et al. | |
| 2013/0131642 A1 | | 5/2013 | Miyata et al. | |

FOREIGN PATENT DOCUMENTS

| | | | | |
|---|---|---|---|---|
| EP | 1938859 B1 | * | 3/2016 | A61M 25/09 |
| JP | H09-294812 A | | 11/1997 | |
| JP | 2005-125100 A | | 5/2005 | |
| JP | 2005-534407 A | | 11/2005 | |
| JP | 2012-200290 A | | 10/2012 | |
| JP | 2012205793 A | | 10/2012 | |
| JP | 2013-085854 A | | 5/2013 | |
| JP | 2013-106854 A | | 6/2013 | |
| JP | 2014-147459 A | | 8/2014 | |
| JP | 201566163 A | | 4/2015 | |

\* cited by examiner

GUIDE WIRE

CROSS-REFERENCES TO RELATED APPLICATIONS

This application claims the benefit of Japanese Application No. 2018-032453 filed on Feb. 26, 2018, the entire content of which is incorporated herein by reference.

TECHNICAL FIELD

The present invention relates to a guide wire.

BACKGROUND

It is known in the medical field to use a guide wire in order to guide a catheter device to a lesion area (for example, stenosed site) formed in a biological lumen. In order to improve deliverability of the guide wire into the biological lumen, it is known to make a distal portion of such guide wires flexible (resilient). For example, according to the guide wire disclosed in JP-A-2012-205793, a coil is located so as to surround a periphery of a distal portion of a core member. In this guide wire, flexibility of the distal portion of the guide wire is improved by locating the coil in the distal portion of the guide wire.

However, issues may arise when the coil is located in the distal portion of the guide wire. For example, in a case where the distal portion of the guide wire is trapped in the lesion area (for example, chronic total occlusion), or in a case where the distal portion of the guide wire is interposed between a stent and a vascular wall (or the lesion area) during a medical procedure of wire protection, and an operator strongly pulls the guide wire to a proximal side or the like, the coil may suffer damage such as breakage and separation (elongation).

A countermeasure to the above-described problem is described in JP-A-2015-66163, in which, instead of the coil, a pipe (a hollow member) having a slit formed therein is located in the distal portion of the guide wire.

However, a pipe is less stretchable than a coil. Thus, in a case where a pipe is used instead of a coil, it is difficult to sufficiently improve flexibility of the distal portion of the guide wire.

SUMMARY

The present disclosure aims to provide a guide wire which is flexible in a distal portion and which can prevent occurrence of damage such as breakage and separation of a coil in the distal portion.

According to the present disclosure, there is provided a guide wire having an elongated core member, and a tubular body located so as to cover a periphery of a distal portion of the core member. The tubular body is formed using a belt-shaped member wound in a spiral shape, and has an engagement portion which causes side portions adjacent in a longitudinal axis direction of the core member to engage with each other in the belt-shaped member.

In the guide wire, the tubular body including the engagement portion which causes the side portions of the belt-shaped member to engage with each other is located so as to cover an outer periphery of the distal portion of the core member. Accordingly, compared to a guide wire including a coil structure, strength (fracture resistant strength) of the distal portion of the guide wire is higher. Therefore, even if the distal portion of the guide wire is caught on a lesion area or a stent, the distal portion of the guide wire is less likely to be damaged. In addition, the guide wire is allowed to be additionally flexible in the distal portion of the guide wire by the belt-shaped member wound around the periphery of the core member. Therefore, compared to a guide wire including a pipe structure, the distal portion of the guide wire is highly flexible.

DETAILED DESCRIPTION

Figure 1:
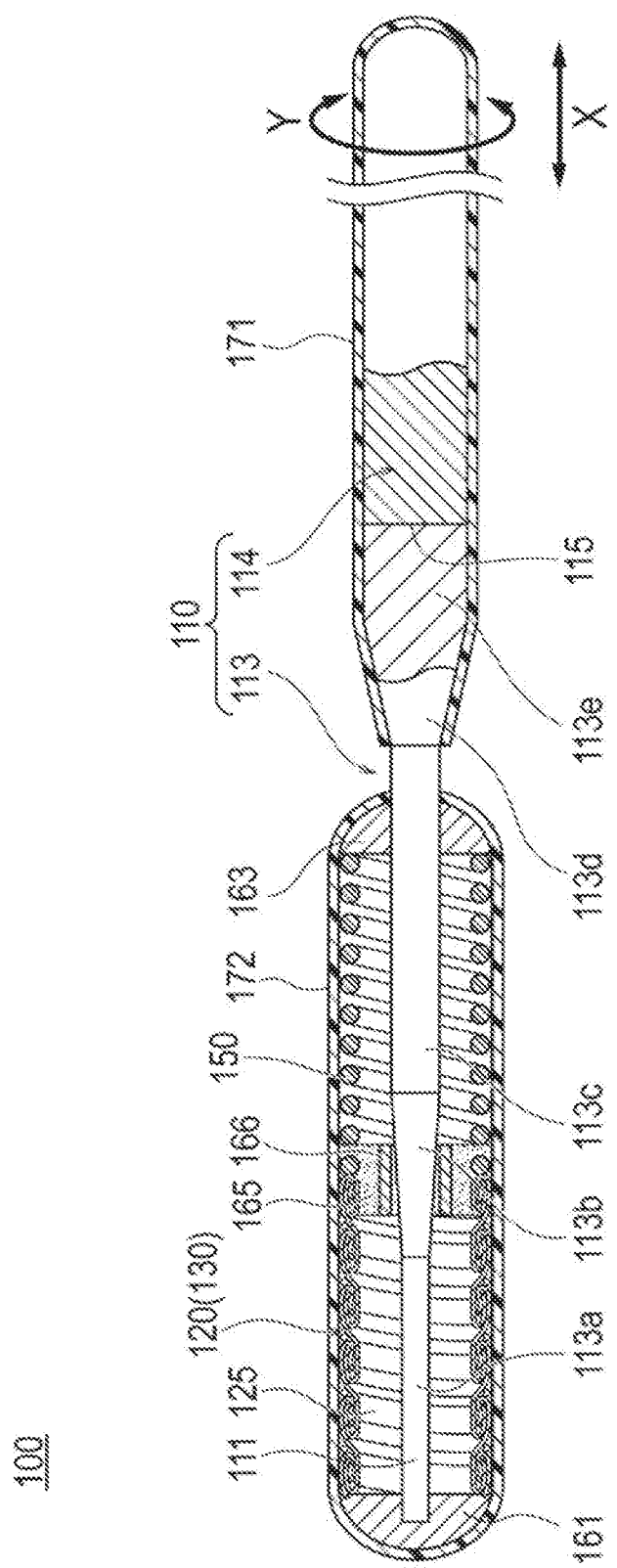
FIG. 1 is a cross-sectional view in an axial direction of a guide wire according to a first embodiment of the present disclosure.

Hereinafter, embodiments according to the present disclosure will be described with reference to the accompanying drawings. In describing the drawings, the same reference numerals will be given to the same elements, and repeated description will be omitted. In addition, dimensional proportions in the drawings are exaggerated and different from actual proportions for convenience of description, in some cases.

Figure 2:
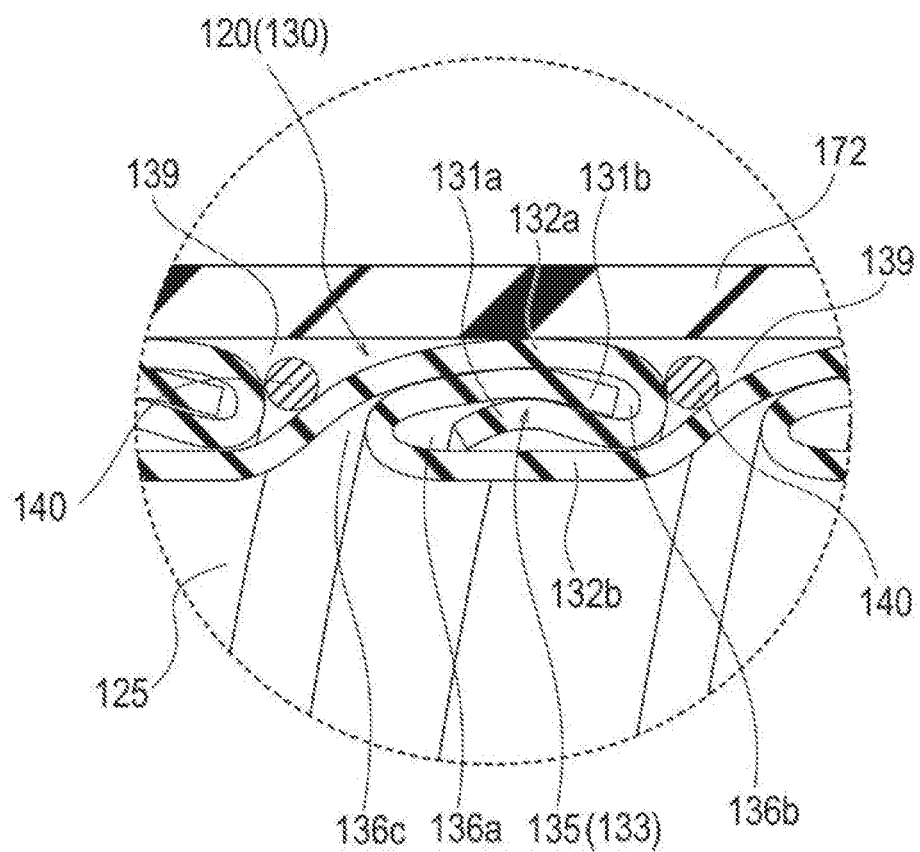
FIG. 2 is an enlarged cross-sectional view illustrating an engagement portion of the guide wire illustrated in FIG. 1.

FIG. 1 is a view illustrating an overall configuration of a guide wire 100 according to the present embodiment. FIG. 2 is a partially enlarged cross-sectional view of a tubular body 120 included in the guide wire 100 according to the present embodiment.

Referring to FIG. 1, in brief, the guide wire 100 has an elongated core member (core wire) 110, the tubular body 120 located so as to cover a periphery of a distal portion 111 of the core member 110, and a coil 150 located closer to a proximal side than the tubular body 120. Hereinafter, each portion of the guide wire 100 will be described in detail.

In the description herein, a direction in which the core member 110 extends in a natural state (a state where no external force is applied and the core member 110 is straightly extended) will be referred to as a "longitudinal axis direction" (arrow X in the drawing). In addition, a rotation direction in which the core member 110 is rotated around the longitudinal axis direction of the core member 110 as a reference axis will be referred to as a "circumferential direction" (arrow Y in the drawing). In addition, in the guide wire 100, a side to be introduced into a living body will be referred to as a distal side (distally located side, left side in FIG. 1), and an end portion side opposite to the distal side will be referred to as a proximal side (proximally located side, right side in FIG. 1). In addition, a portion including a certain range in the longitudinal axis direction from a distal end (most distal end) will be referred to as a "distal portion", and a portion including a certain range in the longitudinal axis direction from a proximal end (most proximal end) will be referred to as a "proximal portion".

[Core Member]

As illustrated in FIG. 1, the core member 110 includes a first core portion 113 located on the distal side in the longitudinal axis direction, and a second core portion 114 located on the proximal side of the first core portion 113 and joined to the first core portion 113.

As illustrated in FIG. 1, the first core portion 113 includes a first constant outer diameter portion 113a extending from the distal side to the proximal side while maintaining a substantially constant outer diameter, a first tapered portion 113b extending from the first constant outer diameter portion 113a to the proximal side, a second constant outer diameter portion 113c extending from the first tapered portion 113b to the proximal side while maintaining a substantially constant outer diameter, a second tapered portion 113d extending from the second constant outer diameter portion 113c to the proximal side, and a third constant outer diameter portion 113e extending from the second tapered portion 113d to the proximal side while maintaining a substantially constant outer diameter.

According to the present embodiment, the first constant outer diameter portion 113a of the first core portion 113 has a round bar-like (columnar) outer shape. However, the first constant outer diameter portion 113a may have a flat plate (prismatic) outer shape. In addition, the first core portion 113 may have a constant outer shape or a constant outer diameter from the distal side to the proximal side, for example.

The component material of the first core portion 113 is not particularly limited. However, for example, it is possible to use a super-elastic alloy such as a Ni—Ti alloy, stainless steel, or a cobalt-based alloy.

As illustrated in FIG. 1, the second core portion 114 is connected to the proximal end of the third constant outer diameter portion 113e of the first core portion 113 via a connection portion 115. The first core portion 113 and the second core portion 114 can be connected to each other by means of welding or soldering, for example.

The component material of the second core portion 114 is not particularly limited. However, for example, it is possible to use a super-elastic alloy such as a Ni—Ti alloy, stainless steel, or a cobalt-based alloy.

A peripheral surface of the proximal portion of the first core portion 113, a peripheral surface of the connection portion 115, and an outer surface of the second core portion 114 are provided with a covering layer 171. The component material of the covering layer 171 is not particularly limited. However, for example, it is possible to use polyolefin such as polyethylene and polypropylene, polyvinyl chloride, polyester (for example, PET or PBT), polyamide, polyimide, polyurethane, polystyrene, polycarbonate, silicone resin, and fluorine-based resin (for example, PTFE or ETFE), or a composite material of these materials. The component material of the covering layer 171 may vary in a portion disposed on the peripheral surface of the proximal portion of the first core portion 113, a portion disposed on the outer surface of the second core portion 114, and a portion disposed on the peripheral surface of the connection portion 115.

The core member 110 may include a single continuous member without including a plurality of members as in the first core portion 113 and the second core portion 114.

[Coil]

The coil 150 is located on the proximal side of the tubular body 120 so as to cover the core member 110 in a certain range in the longitudinal axis direction (range including a portion of the second constant outer diameter portion 113c from the vicinity of the center in the longitudinal axis direction of the first tapered portion 113b). The coil 150 is wound in a spiral shape so that a wire rod covers the outer periphery of the core member 110. The coil 150 is a sparsely wound coil having a clearance formed between wire rods configuring the coil 150. However, the coil 150 may be a densely wound coil having no clearance between the wire rods.

The component material of the coil 150 is not particularly limited. However, for example, it is possible to use stainless steel, a superelastic alloy such as a Ni—Ti alloy, a cobalt-based alloy, metal such as gold, platinum, and tungsten, or an alloy containing these materials.

As illustrated in FIG. 1, the distal end (distal end of the first constant outer diameter portion 113a) of the core member 110 and the distal end of the tubular body 120 are fixed by a distal side fixing portion 161. It is preferable that the distal portion of the distal side fixing portion 161 has a rounded shape as illustrated, in view of the influence on an inner wall (for example, a vascular wall) of a living body in a case where the distal portion comes into contact with the inner wall of the living body.

As illustrated in FIG. 1, an insertion member 166 is located in the vicinity of a central portion in the longitudinal axis direction of the first tapered portion 113b. The distal end of the insertion member 166 is located in a lumen 125 of the tubular body 120, and the proximal end of the insertion member 166 is located in a lumen of the coil 150. The core member 110 is inserted into the insertion member 166. The core member 110, the tubular body 120, and the coil 150 are fixed to the insertion member 166 via an intermediate side fixing portion 165 disposed on an inner peripheral side and an outer peripheral side of the insertion member 166. The insertion member 166 can include a known resin material or a known metal material.

As illustrated in FIG. 1, the second constant outer diameter portion 113c of the core member 110 and the proximal end of the coil 150 are fixed by a proximal side fixing portion 163.

Members in respective portions of the distal side fixing portion 161, the proximal side fixing portion 163, and the intermediate side fixing portion 165 are fixed, for example, using a soldering material, a brazing material, or an adhesive, in view of a material of fixing target members.

As illustrated in FIG. 1, a covering layer 172 is disposed in each member (the tubular body 120, the coil 150, the distal side fixing portion 161, and the proximal side fixing portion 163) located closer to the distal side than the proximal side fixing portion 163 in the guide wire 100. The component material of the covering layer 172 is not particularly limited. However, for example, it is possible to use hydrophilic materials such as a cellulose-based polymer substance, a polyethylene oxide-based polymer substance, a maleic anhydride-based polymer substance (for example, a maleic anhydride copolymer such as a methyl vinyl ether-maleic anhydride copolymer), an acrylamide-based polymer substance (for example, polyacrylamide, glycidyl methacrylate-dimethyl acrylamide block copolymer), water-soluble nylon, polyvinyl alcohol, and polyvinyl pyrrolidone.

[Tubular Body]

As illustrated in FIGS. 1 and 2, the tubular body 120 is formed using a belt-shaped member 130 wound in a spiral shape.

The belt-shaped member 130 includes a single continuous plate-shaped member. The lumen 125 into which the core member 110 is inserted is formed on the inner peripheral side of the wound belt-shaped member 130.

As illustrated in FIG. 2, the tubular body 120 includes an engagement portion 133 that causes a first side portion 131a and a second side portion 131b, adjacent to each other in the longitudinal axis direction of the core member 110, to engage with each other in the belt-shaped member 130.

In the tubular body 120, a set of the side portions 131a and 131b included in the belt-shaped member 130 engage with each other in the engagement portion 133. The first side portion 131a is formed by shaping a portion of the belt-shaped member 130 into a form bent toward the distal side. In addition, the second side portion 131b is formed by shaping a portion of the belt-shaped member 130 into a form bent toward the proximal side.

The first side portion 131a and the second side portion 131b are interposed in a radiation direction of the core member 110 between a portion 132a of the belt-shaped member 130 located on the outer peripheral side of the first side portion 131a and a portion 132b of the belt-shaped member 130 located on the inner peripheral side of the second side portion 131b. In the description herein, the radiation direction of the core member 110 (hereinafter, referred to as the "radiation direction") means a direction away from or close to the core member 110 in an axially orthogonal cross section of the core member 110, based on an axis of the core member 110. For example, in a case where the core member 110 has a circular axially orthogonal cross-sectional shape, the radiation direction of the core member 110 means a radial direction of the core member 110.

The engagement portion 133 includes a holding portion 135 which can generate a frictional force between the first side portion 131a and the second side portion 131b. The tubular body 120 has a plurality of clearance portions 136a, 136b, and 136c disposed adjacent to the holding portion 135 in the longitudinal axis direction.

The inner peripheral surface (upper surface in FIG. 2 which faces the second side portion 131b) of the first side portion 131a and the inner peripheral surface (lower surface in FIG. 2 which faces the first side portion 131a) of the second side portion 131b configure the engagement portion 133 (holding portion 135). The inner peripheral surface of the first side portion 131a and the inner peripheral surface of the second side portion 131b are arranged so as to come into pressure contact with each other. Therefore, when the inner peripheral surface of the first side portion 131a and the inner peripheral surface of the second side portion 131b are relatively moved, a frictional force is generated between the inner peripheral surface of the first side portion 131a and the inner peripheral surface of the second side portion 131b.

The clearance portion 136a is disposed on the distal side (left side in FIG. 2) of the first side portion 131a. The clearance portion 136b is disposed on the proximal side (right side in FIG. 2) of the second side portion 131b. The clearance portion 136c is disposed on the distal side (left side in FIG. 2) of the first side portion 131a and the second side portion 131b.

While maintaining a state where the side portions 131a and 131b of the belt-shaped member 130 engage with each other, the engagement portion 133 and the clearance portions 136a, 136b, and 136c which are included in the tubular body 120 allow the belt-shaped member 130 to move (swing) in the engagement portion 133 serving as a base point.

In addition, in a state where the engagement between the side portions 131a and 131b is maintained by the engagement portion 133 included in the tubular body 120, the clearance portions 136a, 136b, and 136c adjacent to the engagement portion 133 allow the respective side portions 131a and 131b to move in the longitudinal axis direction. The tubular body 120 has a structure (a so-called interlock mechanism) which can cause the tubular body 120 to maintain a deformed shape by using a frictional force generated between the respective side portions 131a and 131b in the engagement portion 133, if the tubular body 120 is deformed (for example, curved or bent).

In the guide wire 100 according to the present embodiment, the distal portion of the guide wire 100 can be shaped by deforming the tubular body 120. In addition, the shape of the distal portion of the guide wire 100 after the shape is formed is maintained by deforming the tubular body 120. Therefore, the guide wire 100 does not need the distal portion of the core member 110 to have a flat plate shape, or be made of a material having a physical property which enables the shaping, in order for shaping of the distal portion to be possible.

As described above, in the guide wire 100, the distal end (first core portion 113) of the core member 110 has a round bar shape (axially orthogonal cross section is circular). In a case where the distal end of the core member 110 has the round bar shape, the distal end of the core member 110 is less likely to maintain a formed shape, compared to a case having a flat plate shape. However, in the guide wire 100, the tubular body 120 has the interlock structure. Accordingly, despite the distal portion of the core member 110 having the round bar shape, the formed shape can be satisfactorily maintained. In addition, in the case where the distal portion of the core member 110 has the round bar shape, the distal portion of the core member 110 is less likely to be twisted, compared to the case having the flat plate shape. Therefore, the guide wire 100 according to the present embodiment can satisfactorily transmit torque applied to the proximal side by an operator, to the distal end of the core member 110.

In the guide wire 100, the tubular body 120 including the engagement portion 133 formed by members meshing with each other is located in the periphery of the distal portion 111 of the core member 110. In addition, in the engagement portion 133 of the guide wire 100, the side portions 131a and 131b of the belt-shaped member 130 in a wound state are mechanically connected to each other. Therefore, in the guide wire 100, for example, a phenomenon is less likely to occur in which wire rods wound like the coil are extended and broken in the longitudinal axis direction. In addition, in the engagement portion 133 of the guide wire 100, the respective side portions 131a and 131b of the belt-shaped member 130 and the predetermined portions 132a and 132b of the belt-shaped member 130 overlap each other in the radiation direction (vertical direction in FIG. 2) of the core member 110. Therefore, in the guide wire 100, mechanical strength of the tubular body 120 is partially higher in the vicinity of the engagement portion 133. Therefore, in the guide wire 100, the strength (fracture resistant strength) of the distal portion of the guide wire 100 is higher, compared to the guide wire including only the coil.

As described above, the guide wire 100 has high strength in the distal portion. Accordingly, for example, even in a case where the outer diameter of the distal portion of the tubular body 120 is reduced, it is possible to preferably prevent damage to the distal portion of the guide wire 100. Therefore, the tubular body 120 may be formed in a tapered shape in which the outer diameter is tapered toward the distal side of the guide wire 100. In the guide wire 100, the tubular body 120 has the tapered shape. Accordingly, the guide wire 100 is delivered to the lesion area (stenosed site) in an improved manner.

In a case of reducing the outer diameter of the distal portion of the guide wire 100, the lumen of the tubular body 120 disposed in the distal portion of the guide wire 100 needs to have a sufficient size (inner diameter) into which the core member 110 can be inserted. If the distal portion of the guide wire includes only a coil, the coil should be formed by winding a wire rod with a narrow outer diameter in order to keep the lumen of the coil at a predetermined size and prevent the distal end of the guide wire from having an excessively large outer diameter. The coil formed by winding a wire rod with a narrow outer diameter has a lowered breakage strength, which can easily cause damage to the distal portion of the guide wire. On the other hand, as described above, the guide wire 100 according to the present embodiment can have a distal portion with a strength (fracture resistant strength) higher than that of the guide wire including only the coil. Therefore, the distal portion of the guide wire 100 can be advantageously prevented from being damaged even when the outer diameter of the distal portion is reduced.

In addition, in a state where the engagement between the side portions 131a and 131b is maintained by the engagement portion 133 included in the tubular body 120, the clearance portions 136a, 136b, and 136c adjacent to the holding portion 135 allow the respective side portions 131a and 131b to move in the longitudinal axis direction. Accordingly, the tubular body 120 is flexible. Therefore, compared to the guide wire including the pipe structure, the flexibility of the distal portion of the guide wire 100 is improved.

In addition, if the distal portion of the guide wire 100 includes only a coil formed by winding a wire rod with a circular cross-sectional shape, the component material (coating agent) of the covering layer 172 may enter the clearance between the wire rod portions that form the coil, so that an area of the coating layer 172 capable of coming into contact with the inner wall of the living body may decrease. In the guide wire 100 according to the present embodiment, the tubular body 120 formed using the spirally wound belt-shaped member 130 is located in the distal portion of the guide wire 100. The belt-shaped member 130 includes a plate-shaped member, so that an area of the tubular body 120 capable of coming into contact with the inner wall of the living body will be larger than that of the coil. Therefore, the guide wire 100 can hold a larger amount of the covering layer 172 in the distal portion of the guide wire 100, which improves slidability and the like.

The component material of the tubular body 120 (belt-shaped member 130) is not particularly limited. However, for example, it is possible to use a radiopaque material including metal such as gold, platinum, and tungsten, and an alloy containing these materials, or metal such as stainless steel, a superelastic alloy such as Ni—Ti alloy, and a cobalt-based alloy, and a radioparent material such as a polymer material including polytetrafluoroethylene, polyurethane, silicone, and polyimide.

As illustrated in FIG. 2, the guide wire 100 has a wire rod 140 wound around the outer peripheral side of the belt-shaped member 130.

The wire rod 140 is wound in a spiral shape along the outer periphery of the belt-shaped member 130. The wire rod 140 is located in a clearance portion 139 formed between the side portions adjacent to each other in the longitudinal axis direction (between a set of the side portions 131a and 131b adjacent to each other). For example, the wire rod 140 may include one having a circular cross-sectional shape. The component material of the wire rod 140 is not particularly limited. However, for example, it is possible to use a material the same as the component material of the tubular body 120 (belt-shaped member 130).

The guide wire 100 may have a sealing member (for example, cotton yarn) in any desired clearance portion in the vicinity of the engagement portion 133 of the tubular body 120.

As described above, the guide wire 100 according to the present embodiment has the elongated core member 110, and the tubular body 120 located so as to cover the periphery of the distal portion 111 of the core member 110. The tubular body 120 is formed using the belt-shaped member 130 wound in a spiral shape, and has the engagement portion 133 which causes the side portions 131a and 131b which are adjacent to each other in the longitudinal axis direction of the core member 110 to engage with each other in the belt-shaped member 130.

In the guide wire 100 configured as described above, the tubular body 120 including the engagement portions 133 that causes the side portions 131a and 131b of the belt-shaped member 130 to engage with each other is located so as to cover the outer periphery of the distal portion of the core member 110. Accordingly, compared to the guide wire including the coil structure, the strength (fracture resistant strength) of the distal portion of the guide wire 100 is high. Therefore, according to the guide wire 100, even if the distal portion of the guide wire 100 is caught on the lesion area or the stent, the distal portion of the guide wire 100 is less likely to be damaged. In addition, the guide wire 100 is allowed to be additionally flexible in the distal portion of the guide wire 100 by the belt-shaped member 130 wound around the periphery of the core member 110. Therefore, according to the guide wire 100, compared to the guide wire including the pipe structure, the distal portion of the guide wire 100 is highly flexible.

In addition, the engagement portion 133 in the guide wire 100 includes the holding portion 135 which generates a frictional force between the respective side portions 131a and 131b. The tubular body 120 has the clearance portions 136a, 136b, and 136c disposed adjacent to the holding portion 135 in the longitudinal axis direction. In a state where the engagement between the side portions 131a and 131b is maintained by the engagement portion 133 included in the tubular body 120, the clearance portions 136a, 136b, and 136c adjacent to the holding portion 135 allow the respective side portions 131a and 131b to move in the longitudinal axis direction. In the guide wire 100, if the tubular body 120 is deformed (for example, curved or bent), the tubular body 120 is allowed to maintain a deformed shape by using a frictional force generated between the respective side portions 131a and 131b in the holding portion 135 of the tubular body 120. Therefore, the guide wire 100 can preferably maintain a predetermined shape formed by the operator.

In addition, the guide wire 100 further has the wire rod 140 wound around the outer peripheral side of the belt-shaped member 130. When the tubular body 120 is curved, the wire rod 140 limits a curve range of the tubular body 120 between a set of the side portions 131a and 131b adjacent to each other. Therefore, the guide wire 100 can define a bend radius of the belt-shaped member 130, and can prevent the belt-shaped member 130 from being excessively bent and damaged.

In addition, the guide wire 100 has the coil 150 located so as to cover the periphery of the core member 110. The coil 150 is located closer to the proximal side than the tubular body 120. Therefore, the guide wire 100 can prevent damage to the distal portion of the guide wire 100 by using the tubular body 120, and the flexibility of the guide wire 100 closer to the proximal side than the tubular body 120 can be preferably improved by the coil 150.

Next, modification examples of the tubular body 120 described in the first embodiment will be described. The same reference numerals will be given to the previously described configurations, and description thereof will be omitted. In the following respective modification examples, a structure example (structure example of an interlock mechanism) of an engagement portion of a tubular body will be described. In each drawing illustrating the modification example, the covering layer 172 will be omitted in the illustration.

Modification Example 1

Figure 3A:
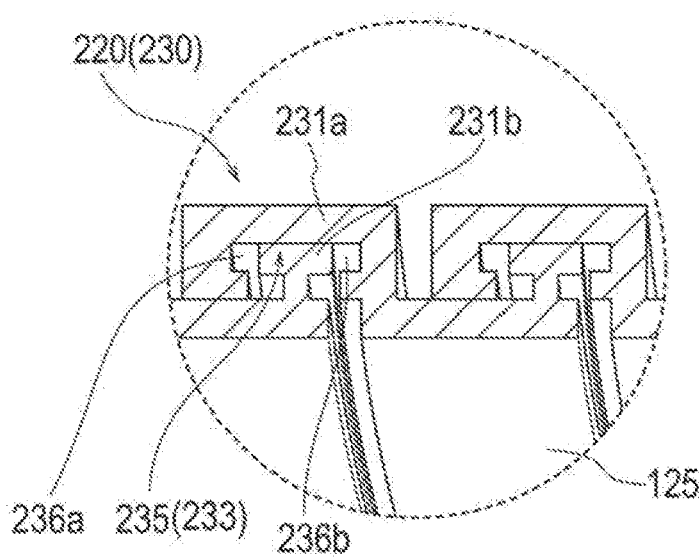
FIG. 3(A) is an enlarged cross-sectional view illustrating Modification Example 1 of the engagement portion of the guide wire according to the first embodiment.

As illustrated in FIG. 3(A), a tubular body 220 according to Modification Example 1 is formed using a belt-shaped member 230. The tubular body 220 has an engagement portion 233. The engagement portion 233 includes a holding portion 235 which generates a frictional force between respective side portions 231a and 231b of the belt-shaped member 230. The tubular body 220 has clearance portions 236a and 236b adjacent to the holding portion 235.

The first side portion 231a of the belt-shaped member 230 has a space portion for accommodating the second side portion 231b of the belt-shaped member 230. An upper end portion of the second side portion 231b is located so as to be always in contact with an inner wall surface of the first side portion 231a. The second side portion 231b is movable in the longitudinal axis direction by the respective clearance portions 236a and 236b adjacent to the holding portion 235 (contact location between the first side portion 231a and the second side portion 231b).

Similar to the tubular body 120 according to the above-described first embodiment, if the tubular body 220 is deformed (for example, curved or bent), the tubular body 220 according to Modification Example 1 can maintain a deformed shape of the tubular body 220 by using a frictional force generated between the respective side portions 231a and 231b in the holding portion 235. Therefore, after the shape is formed by the operator or the like, the tubular body 220 can satisfactorily maintain the shape of the distal portion of the shaped guide wire.

Modification Example 2

Figure 3B:
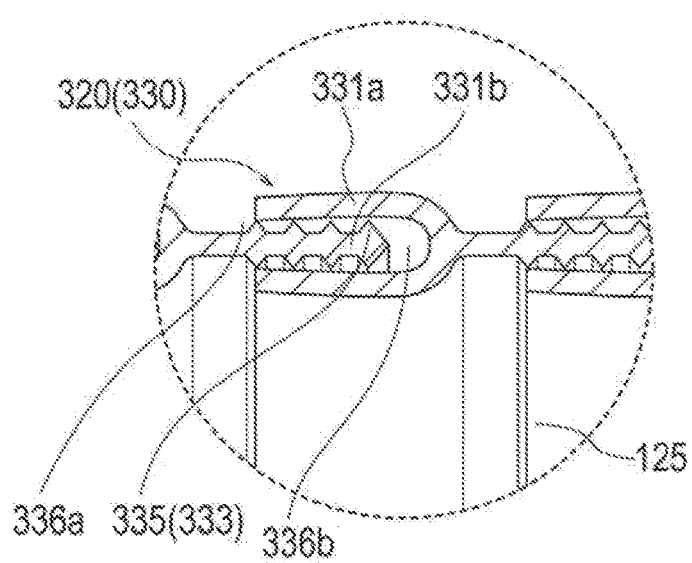
FIG. 3(B) is an enlarged cross-sectional view illustrating Modification Example 2 of the engagement portion of the guide wire according to the first embodiment.

As illustrated in FIG. 3(B), a tubular body 320 according to Modification Example 2 is formed using a belt-shaped member 330. The tubular body 320 has an engagement portion 333. The engagement portion 333 includes a holding portion 335 which generates a frictional force between respective side portions 331a and 331b of the belt-shaped member 330. The tubular body 320 has clearance portions 336a and 336b adjacent to the holding portion 335.

The first side portion 331a of the belt-shaped member 330 has a space portion for accommodating the second side portion 331b of the belt-shaped member 330. The second side portion 331b has a plurality of convex portions functioning as the holding portion 335. The holding portion 335 generates a frictional force between the holding portion 335 and the first side portion 331a by coming into contact with the inner wall surface of the first side portion 331a. The second side portion 331b is movable in the longitudinal axis direction by using the clearance portions 336a and 336b adjacent to the holding portion 335.

Similar to the tubular body 120 according to the above-described first embodiment, if the tubular body 320 is deformed (for example, curved or bent), the tubular body 320 according to Modification Example 2 can maintain a deformed shape of the tubular body 320 by using a frictional force generated between the respective side portions 331a and 331b in the holding portion 335. Therefore, after the shape is formed by the operator or the like, the tubular body 320 can satisfactorily maintain the shape of the distal portion of the shaped guide wire.

Modification Example 3

Figure 3C:
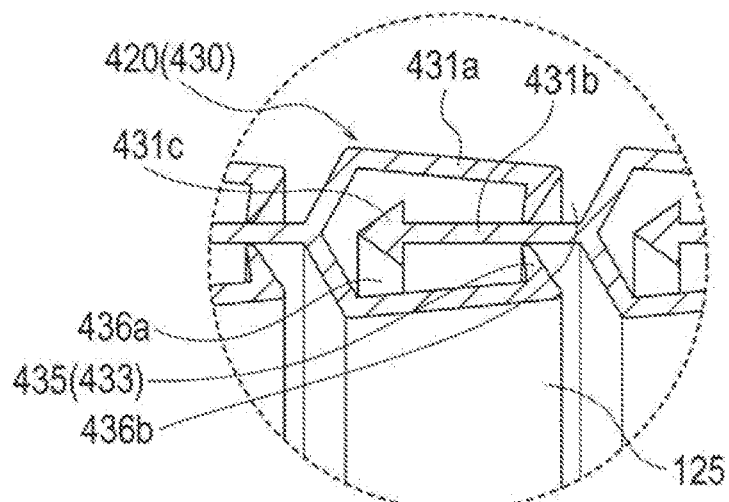
FIG. 3(C) is an enlarged cross-sectional view illustrating Modification Example 3 of the engagement portion of the guide wire according to the first embodiment.

As illustrated in FIG. 3(C), a tubular body 420 according to Modification Example 3 is formed using a belt-shaped member 430. The tubular body 420 has an engagement portion 433. The engagement portion 433 includes a holding portion 435 which generates a frictional force between respective side portions 431a and 431b of the belt-shaped member 430. The tubular body 420 has clearance portions 436a and 436b adjacent to the holding portion 435.

The first side portion 431a of the belt-shaped member 430 has a space portion for accommodating the second side portion 431b of the belt-shaped member 430. The first side portion 431a has a pinching portion functioning as the holding portion 435. The holding portion 435 generates a frictional force between the first side portion 431a and the second side portion 431b by pinching the second side portion 431b while coming into contact with the second side portion 431b. The second side portion 431b is movable in the longitudinal axis direction by using the clearance portions 436a and 436b adjacent to the holding portion 435. The distal side (left side in the drawing) of the second side portion 431b has a convex portion 431c which prevents the second side portion 431b from slipping out of the first side portion 431a.

Similar to the tubular body 120 according to the above-described first embodiment, if the tubular body 420 is deformed (for example, curved or bent), the tubular body 420 according to Modification Example 3 can maintain a deformed shape of the tubular body 420 by using a frictional force generated between the respective side portions 431a and 431b in the holding portion 435. Therefore, after the shape is formed by the operator or the like, the tubular body 420 can satisfactorily maintain the shape of the distal portion of the shaped guide wire.

Second Embodiment

Next, a guide wire according to a second embodiment will be described. The same reference numerals will be given to configuration the same as those of the first embodiment, and description thereof will be omitted.

Figure 4:
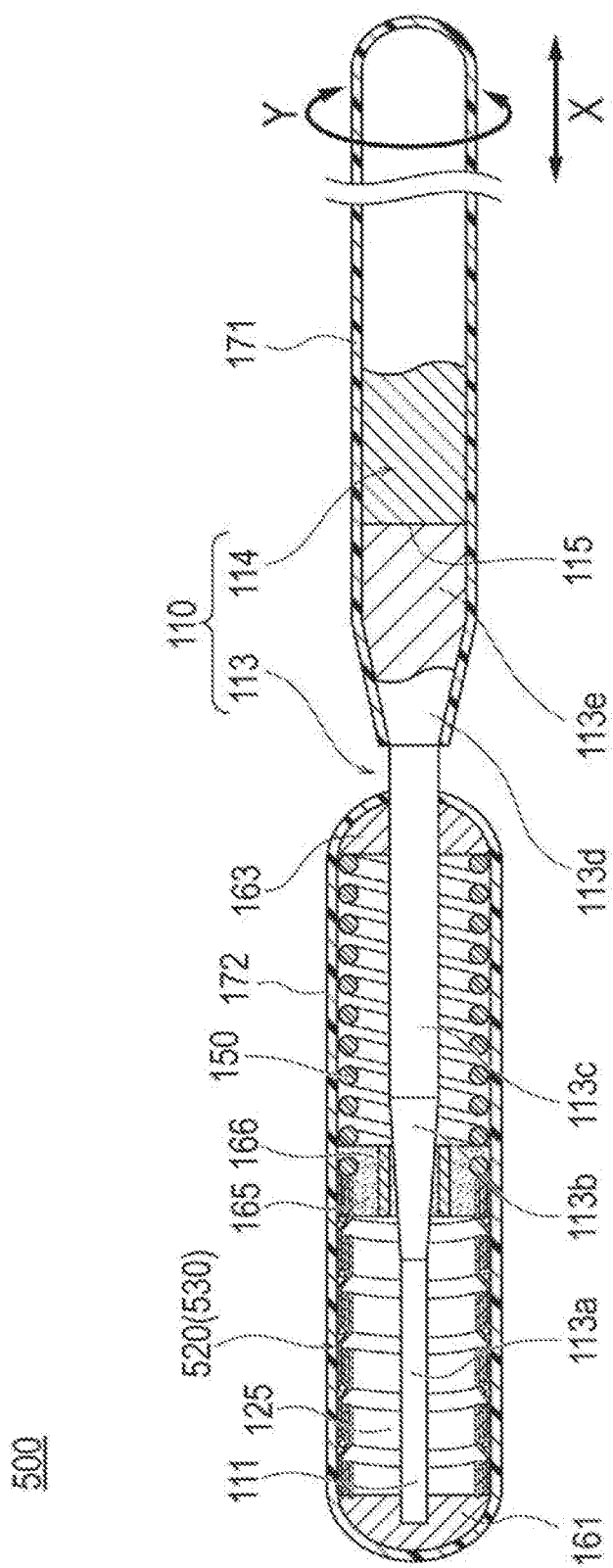
FIG. 4 is a cross-sectional view in the axial direction of a guide wire according to a second embodiment of the present disclosure.
Figure 5:
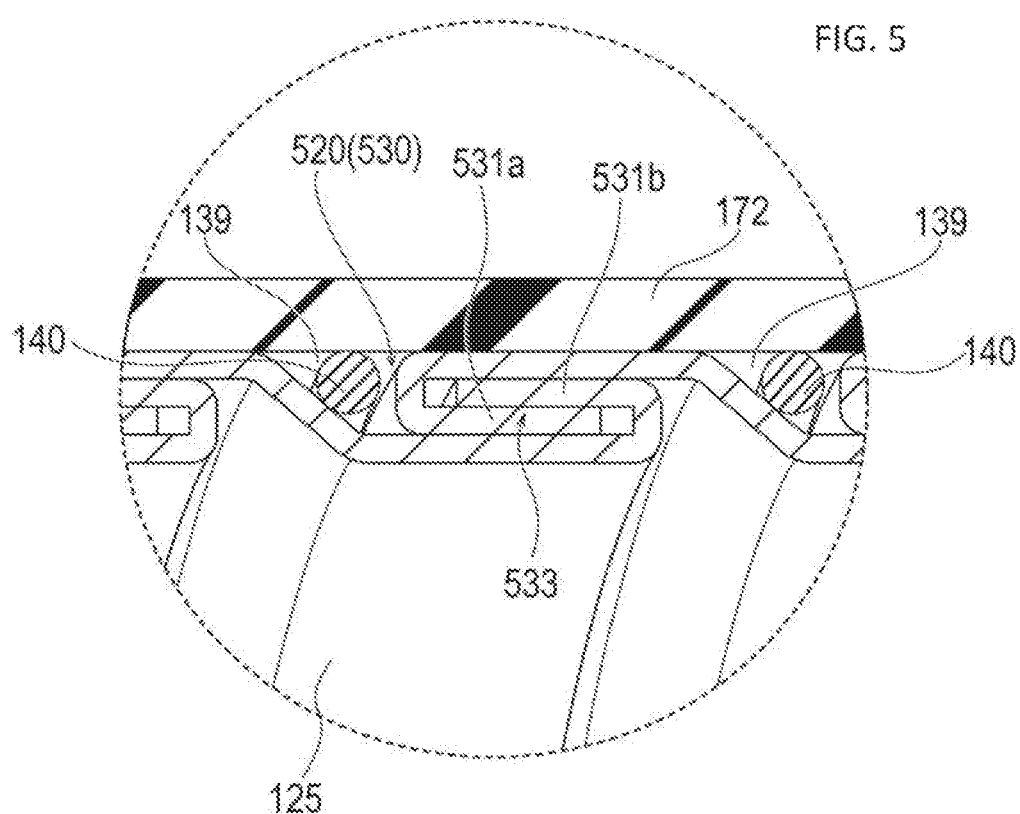
FIG. 5 is an enlarged cross-sectional view illustrating an engagement portion of the guide wire according to the second embodiment.

As illustrated in FIGS. 4 and 5, a configuration of a tubular body 520 in a guide wire 500 according to the second embodiment is different from that of the guide wire 100 according to the first embodiment. As illustrated in FIG. 5, in a belt-shaped member 530 forming the tubular body 520, side portions 531a and 531b engage with each other so as to be in close contact with each other in an engagement portion 533. Here, the term of "close contact" means that no clearance portion exists between the first side portion 531a and the second side portion 531b in the radiation direction (vertical direction in FIG. 5), or means that a size of the clearance portion is slight.

The tubular body 120 according to the above-described first embodiment has the structure (interlock mechanism) for maintaining the formed shape by using the engagement portion (holding portion 135) and the clearance portions 136a, 136b, and 136c. On the other hand, the engagement portion 533 according to the present embodiment does not include the holding portion which generates a frictional force between the respective side portions 531a and 531b. The tubular body 520 according to the present embodiment has a structure (so-called semi-interlock mechanism) which cannot sufficiently maintain the formed shape.

In addition, the first constant outer diameter portion 113a of the core member 110 according to the present embodiment is formed in a flat plate (prismatic) outer shape.

In the guide wire 500 according to the second embodiment, the side portions 531a and 531b of the belt-shaped member 530 engage with each other so as to be in close contact with each other in the engagement portion 533 of the tubular body 520. Even in a case where the tubular body 520 is deformed (for example, curved or bent), in the guide wire 500 having this engagement portion 533, the tubular body 520 is less likely to maintain a deformed shape. In the guide wire 500, each position of the respective side portions 531a and 531b in the engagement portion 533 is not restricted before and after the tubular body 520 is deformed. Accordingly, the flexibility of the distal portion of the guide wire 500 is further improved.

The distal portion 111 (first constant outer diameter portion 113a) of the core member 110 included in the guide wire 500 according to the second embodiment has a flat plate shape. Therefore, compared to a case where the distal portion 111 of the core member 110 includes a round bar-shaped member, the guide wire 500 can advantageously maintain a predetermined shape formed by the operator. The guide wire 500 according to the present embodiment is configured so that the tubular body 520 is less likely to maintain the formed shape. However, the core member 110 maintains the formed shape. Accordingly, it is possible to preferably maintain a shape provided for the guide wire 500.

Next, a modification example of the tubular body 520 described in the second embodiment will be described. The same reference numerals will be given to the previously described configurations, and description thereof will be omitted. In the following modification example, a structure example (structure example of the semi-interlock mechanism) of an engagement portion of a tubular body will be described. In each drawing illustrating the modification example, the covering layer 172 will be omitted in the illustration.

Modification Example

Figure 6:
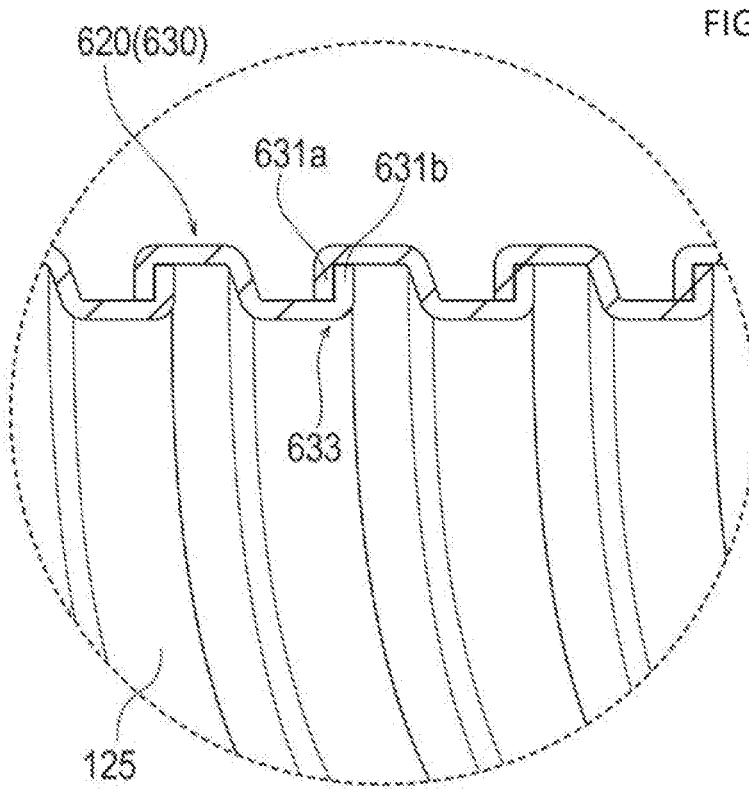
FIG. 6 is an enlarged cross-sectional view illustrating a modification example of the engagement portion of the guide wire according to the second embodiment.

As illustrated in FIG. 6, a tubular body 620 according to the modification example is formed using a belt-shaped member 630. The tubular body 620 has an engagement portion 633. In the belt-shaped member 630, a first side portion 631a and a second side portion 631b in the engagement portion 633 engage with each other so as to be partially in close contact with each other in both directions of the radiation direction (vertical direction in the drawing) and the longitudinal axis direction (lateral direction in the drawing).

Similar to the tubular body 520 according to the above-described second embodiment, even in a case where the tubular body 620 is deformed (for example, curved or bent), the tubular body 620 according to the modification example is less likely to maintain a deformed shape of the tubular body 620. Therefore, in the guide wire, each position of the respective side portions 631a and 631b in the engagement portion 633 is not restricted before and after the tubular body 620 is deformed. Accordingly, the flexibility of the distal portion of the guide wire is improved.

Hitherto, the guide wire according to the present invention has been described with reference to the embodiments. However, the present invention is not limited only to the described configurations, and can be appropriately modified, based on the appended claims.

A specific shape (for example, a cross-sectional shape) of the engagement portion belonging to the belt-shaped member is not particularly limited, as long as the engagement portion has a configuration which enables the adjacent side portions of the belt-shaped member to engage with each other. In addition, the coil for covering the core member may be omitted.

The distal portion of the core member according to the first embodiment may be formed in a flat plate shape. In a case where the distal portion of the core member according to the first embodiment is formed in the flat plate shape, the guide wire can more preferably maintain a formed shape by using the core member and the tubular body. In addition, the distal portion of the core member according to the second embodiment may be formed in a round bar shape.

The detailed description above describes a guide wire disclosed by way of example. The invention is not limited, however, to the precise embodiment and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A guide wire comprising:
an elongated core member;
a tubular body located so as to cover a periphery of a distal portion of the core member, wherein the tubular body is formed using a belt-shaped member wound in a spiral shape, such that side portions of the belt-shaped member adjacent to each other in a longitudinal axis direction of the core member engage with each other, a first side portion of the side portions is bent toward a distal side of the guide wire, and a second side portion of the side portions is bent toward a proximal side of the guide wire; and
a coil located so as to cover a periphery of a portion of the core member proximal to the distal portion, wherein the coil has non-interlocking adjacent loops and extends further proximally than the tubular body.

2. The guide wire according to claim 1,
wherein a frictional force is generated between portions of the side portions, and
a clearance between the side portions is disposed adjacent to the portions of the side portions between which the frictional force is generated in the longitudinal axis direction.

3. The guide wire according to claim 1,
wherein in the belt-shaped member, the side portions engage with each other so as to be in close contact with each other.

4. The guide wire according to claim 1, further comprising:
   a wire rod wound around an outer peripheral side of the belt-shaped member.
5. The guide wire according to claim 1,
   wherein the distal portion of the core member is flat-plate shaped.
6. The guide wire according to claim 1, wherein:
   the core member, a proximal end of the tubular body, and a distal end of the coil are fixed to one another at a first portion of the guide wire;
   the core member and a distal end of the tubular body are fixed to one another at a second portion of the guide wire distal to the first portion; and
   the core member and a proximal end of the coil are fixed to one another at a third portion of the guide wire proximal to the first portion.
7. A guide wire comprising:
   an elongated core member;
   a tubular body covering a periphery of a distal portion of the core member; and
   a coil covering a periphery of a portion of the core member proximal to the distal portion of the core member; wherein
   the core member, a proximal end of the tubular body, and a distal end of the coil are fixed to one another at a first portion of the guide wire,
   the tubular body is formed using a belt-shaped member wound in a spiral shape, such that side portions of the belt-shaped member adjacent to each other in a longitudinal axis direction of the core member engage with each other, a first side portion of the side portions is bent toward a distal side of the guide wire, and a second side portion of the side portions is bent toward a proximal side of the guide wire, and
   the coil has non-interlocking adjacent loops.
8. The guide wire of claim 7, wherein:
   the core member and a distal end of the tubular body are fixed to one another at a second portion of the guide wire distal to the first portion; and
   the core member and a proximal end of the coil are fixed to one another at a third portion of the guide wire proximal to the first portion.
9. The guide wire according to claim 7,
   wherein a frictional force is generated between portions of the side portions, and
   a clearance between the side portions is disposed adjacent to the portions of the side portions between which the frictional force is generated in the longitudinal axis direction.
10. The guide wire according to claim 7,
    wherein in the belt-shaped member, the side portions engage with each other so as to be in close contact with each other.
11. The guide wire according to claim 7, further comprising:
    a wire rod wound around an outer peripheral side of the belt-shaped member.
12. The guide wire according to claim 7,
    wherein the distal portion of the core member is flat-plate shaped.
13. The guide wire according to claim 1,
    wherein the first side portion and the second side portion are interposed, in a radial direction of the core member, between a portion of the belt-shaped member located radially outward of the side portions and a portion of the belt-shaped member located radially inward of the side portions.
14. The guide wire according to claim 7,
    wherein the first side portion and the second side portion are interposed, in a radial direction of the core member, between a portion of the belt-shaped member located radially outward of the side portions and a portion of the belt-shaped member located radially inward of the side portions.
15. The guide wire according to claim 1,
    wherein the first side portion and the second side portion form, in an axial cross-section of the guide wire, respective C-shapes which face in opposite directions.
16. The guide wire according to claim 7,
    wherein the first side portion and the second side portion form, in an axial cross-section of the guide wire, respective C-shapes which face in opposite directions.
17. The guide wire according to claim 1,
    wherein the coil is made from a wire having a circular cross-section.
18. The guide wire according to claim 7,
    wherein the coil is made from a wire having a circular cross-section.

* * * * *